(12) United States Patent
Prins et al.

(10) Patent No.: US 9,291,533 B2
(45) Date of Patent: Mar. 22, 2016

(54) FILTER SUPPORT WITH A PHASE-CHANGING MEDIUM

(75) Inventors: Menno Willem Jose Prins, Rosmalen (NL); Mikhail Mikhaylovich Ovsyanko, Eindhoven (NL); Freek Van Hemert, Dordrecht (NL); Arie Rombertus Van Doorn, Zaltbommel (NL)

(73) Assignee: Koninklijke Philips N.V., Eindhoven (NL)

( * ) Notice: Subject to any disclaimer, the term of this patent is extended or adjusted under 35 U.S.C. 154(b) by 55 days.

(21) Appl. No.: 14/131,757

(22) PCT Filed: Jul. 4, 2012

(86) PCT No.: PCT/IB2012/053408
§ 371 (c)(1),
(2), (4) Date: Jan. 9, 2014

(87) PCT Pub. No.: WO2013/008142
PCT Pub. Date: Jan. 17, 2013

(65) Prior Publication Data
US 2014/0147883 A1 May 29, 2014

Related U.S. Application Data

(60) Provisional application No. 61/507,315, filed on Jul. 13, 2011.

(30) Foreign Application Priority Data

Jul. 18, 2011 (EP) ..................................... 11174313

(51) Int. Cl.
*G02B 21/34* (2006.01)
*G01N 1/28* (2006.01)
*G01N 1/30* (2006.01)
*G01N 1/36* (2006.01)
*G01N 33/569* (2006.01)
*G01N 33/48* (2006.01)

(52) U.S. Cl.
CPC ................. *G01N 1/30* (2013.01); *G01N 1/2813* (2013.01); *G01N 1/36* (2013.01); *G01N 33/48* (2013.01); *G01N 33/569* (2013.01); *G02B 21/34* (2013.01)

(58) Field of Classification Search
None
See application file for complete search history.

(56) References Cited

U.S. PATENT DOCUMENTS

| 5,547,571 | A | 8/1996 | Tsubakino | |
|---|---|---|---|---|
| 2008/0057573 | A1* | 3/2008 | Hutchins et al. | ............ 435/307.1 |
| 2009/0011399 | A1* | 1/2009 | Fischer | .......................... 435/1.1 |

FOREIGN PATENT DOCUMENTS

| DE | 2928790 | 2/1981 |
|---|---|---|
| DE | 3023849 | 1/1982 |

(Continued)

OTHER PUBLICATIONS

Huber, K. C. and BeMiller, J. N., Channels of maize and sorghum starch granules, 2000, Carbohydrate Polymers, vol. 41, pp. 269-276.*

*Primary Examiner* — Ralph Gitomer
*Assistant Examiner* — Trent Clarke

(57) ABSTRACT

The present invention relates to a method for processing isolated cells, in particular rare cells such as circulating tumor cells, to render them suitable for optical imaging, comprising the steps of (a) depositing filter material comprising captured cells on a phase-change medium; (b) melting said phase-change medium until the medium is spread out below said filter material; and (c) lowering the temperature of said phase-change medium until the medium solidifies, resulting in an optically flat filter comprising said cells at a fixed position. The method may additionally comprise an initial step of capturing a cell on a filter material. The phase-change medium, preferably paraffin wax, may comprise a porous, or mesh-like structure allowing the passage of a fluid through the medium. The phase-change medium may further be mounted on a carrier such as a glass carrier or a polymer material carrier. The present invention further relates to processed filter material comprising isolated cells suitable for optical imaging, which is obtainable by the method; the use of such filter material for diagnostic, histological, microbiological, biochemical, oncologic, or hematologic analysis, as well as a device for isolating cells or processing cells to render them suitable for optical imaging.

13 Claims, 5 Drawing Sheets

(56) References Cited

FOREIGN PATENT DOCUMENTS

| DE | 3319678 | 12/1984 |
| DE | 4117833 | 12/1992 |
| EP | 0122581 | 10/1984 |
| WO | WO9005320 | 5/1990 |
| WO | WO2004041994 | 5/2004 |

\* cited by examiner

FILTER SUPPORT WITH A PHASE-CHANGING MEDIUM

CROSS-REFERENCE TO PRIOR APPLICATIONS

This application is the U.S. National Phase application under 35 U.S.C. §371 of International Application Serial No. PCT/IB2012/053408, filed on Jul. 4, 2012, which claims the benefit of European Application Serial No. 11174313.4, filed on Jul. 18, 2011 and U.S. application Ser. No. 61/507,315, filed Jul. 13, 2011. These applications are hereby incorporated by reference herein.

FIELD OF THE INVENTION

The present invention relates to a method for processing isolated cells, in particular rare cells such as circulating tumor cells, to render them suitable for optical imaging, comprising the steps of (a) depositing filter material comprising captured cells on a phase-change medium; (b) melting said phase-change medium until the medium is spread out below said filter material; and (c) lowering the temperature of said phase-change medium until the medium solidifies, resulting in an optically flat filter comprising said cells at a fixed position. The method may additionally comprise an initial step of capturing a cell on a filter material. The phase-change medium, preferably paraffin wax, may comprise a porous, or mesh-like structure allowing the passage of a fluid through the medium. The phase-change medium may further be mounted on a carrier such as a glass carrier or a polymer material carrier. The present invention further relates to processed filter material comprising isolated cells suitable for optical imaging, which is obtainable by the method; the use of such filter material for diagnostic, histological, microbiological, biochemical, oncologic, or hematologic analysis, as well as a device for isolating cells or processing cells to render them suitable for optical imaging.

BACKGROUND OF THE INVENTION

Metastasis, i.e. the spread of cancer from a primary site to non-adjacent secondary sites is one of the major challenges of cancer research, diagnosis and treatment. Metastasis is believed to develop through a series of steps including localized invasion, intravasation, transport through circulation, arrest in microvessels, extravasation, formation of micrometastasis, dormancy, angiogenesis, colonization and formation of macrometastasis (Weinberg, 2007, The biology of cancer, Garland Science, New York). During their transport in the circulatory system, in particular in the blood stream, the tumor cells are referred to as circulating tumor cells (CTC). CTC are considered to play a critical role in the metastatic spread of carcinomas, i.e. of malignancies of the epithelium. Their detection has thus important prognostic and therapeutic implications and is associated inter alia with clinical stage, disease recurrence, treatment response and patient survival. CTC are further seen as independent surrogate markers for the assessment of risk of relapse and the course of treatment.

However, CTC are extremely rare in the bloodstream and are found only with a frequency of 1-10 cells per ml of whole blood in patients with metastatic diseases, in comparison to $10^9$ red blood cells and several million white blood cells, which can be found in the same volume. It is therefore necessary to select and enrich these rare circulating tumor cells. Traditionally, the enrichment process was based on density differences of the CTC, which were separated by density centrifugation. Though, recovery rates are very poor. More recently, the enrichment of CTC was based on the identification of specific surface markers, in particular epithelial adhesion molecule (EpCAM). CTC can accordingly be enriched immuno-magnetically, e.g. by means of ferrofluidic nanoparticles. Yet, this approach is hampered by a broad recovery range of about 10 to 90%, which is apparently due to the variable expression of surface markers (Zheng et al., 2011, Biomed Microdevices, 13: 203-213).

As alternative for the isolation of CTC the use of cell size exclusion methods has been proposed, in particular due to the fact that CTC are as epithelial cells in many cases larger than the surrounding blood cells. Several filter types have been developed including polycarbonate filters comprising pores at random locations, microfabricated filters, microfabricated single layer 2D filters, microfluidic filters based on electric fields, filters microcavity array devices based on nickel electroforming or 3D microfilter devices (Zheng et al., 2011, Biomed Microdevices, 13: 203-213). Similar approaches have also been developed for the selection of other cell types, e.g. bacterial cells within the blood stream or within certain sample forms, bone marrow cells or spleen cells etc.

However, the selection of specific cells from a solution is only the first step of a sequence of reactions necessary to determine the cells' properties, e.g. their metastatic characteristics. Thus, after having been isolated, the cells are typically subjected to staining and optical differentiation procedures. The filter material during these subsequent steps is generally difficult to handle, thin, fragile, and may break easily.

In addition, filters are often corrugated and not optically flat, thus complicating the process of optical imaging of the cells. Although the prior art provides approaches to overcome this problem, e.g. by using immuno-magnetic beads and magnets to pull cells against a microscope cover, the methods are complex, time-consuming or necessitate specialized equipment.

There is hence a need to provide means and methods, which allow for handling of filter material comprising isolated cells such that the captured cells can rapidly and accurately be imaged on the filter material.

OBJECTS AND SUMMARY OF THE INVENTION

The present invention addresses these needs and provides means and methods for processing isolated cells to render them suitable for optical imaging. The above objective is in particular accomplished by a method for processing isolated cells to render them suitable for optical imaging, comprising the steps of (a) depositing filter material comprising captured cells on a phase-change medium; (b) melting said phase-change medium until the medium is spread out below said filter material; and (c) lowering the temperature of said phase-change medium until the medium solidifies, resulting in an optically flat filter comprising said cells at a fixed position. The method provides the advantage that filterable cells such as circulating tumor cells can be processed for subsequent optical analysis steps in a simple, time-saving and accurate manner. The cells have, in particular, been found to be imageable with a very high contrast in standard bright field microscopes, even without any staining. The explanation for the observed high quality properties of processed cells is that the medium scatters light and suppresses reflections from the filter material, the optical components and the supporting material. The present method thus establishes an optically flat filter surface in a very gentle manner. Moreover, the processed cells on the filter are still accessible to staining, fixation, biological or mechanical manipulation or culturing approaches. In addition, a deformation of the surface area during subsequent handling steps can be avoided by a fixation on carrier materials such as glass. The developed methodology is thus very well adapted for the processing of cell types derivable from blood samples, in particular CTCs. In addition, it can generally be applied to any situation, in which cells (of whatever provenience, type or size) are present on a filter material, e.g. cells requiring a subsequent optical analysis.

In a preferred embodiment of the present invention the method as defined above additionally comprising the initial step of capturing a cell on a filter material.

In a further preferred embodiment of the present invention said filter material is capable of size excluding cells to be isolated from a fluid or solution. The filter material may preferably have a pore size of about 0.5 to 20 μm, more preferably of about 8 μm. In further preferred embodiments of the present invention said filter material as defined above is a polymer filter, more preferably a polycarbonate, a parylene or a nylon filter. In yet another preferred embodiment of the present invention said filter material as defined above is a non-polymer filter, more preferably a silicon filter. In yet another preferred embodiment of the present invention said filter material is a 3D microfilter.

In another preferred embodiment of the present invention said phase-change medium is a medium which melts and solidifies in a temperature range of about 25° C. to 70° C.

In a further preferred embodiment the phase-change medium as mentioned above comprises a porous, mesh-like, open, or partially open structure and/or comprises channel, passage or pipe elements, wherein said structure or elements allow the passage of a fluid through said medium.

In yet another preferred embodiment of the present invention said phase-change medium is a hydrocarbon wax, preferably a paraffin wax having a molecular formula of $C_nH_{2n+2}$ with n=20 to 40.

In yet another preferred embodiment of the present invention, said phase-change medium as mentioned above is mounted on a carrier. In a particularly preferred embodiment of the present invention, said carrier is a glass carrier or a polymer material carrier. In a further preferred embodiment said carrier, e.g. glass or polymer material carrier comprises a position marker.

In a further preferred embodiment the method as described herein above comprises as additional step an activity selected from the group of staining, fixating, releasing, mechanically manipulating, biologically manipulating and biochemically manipulating the isolated cell(s).

In a particularly preferred embodiment of the present invention said activity comprises culturing said isolated cell(s), preferably via flowing a nutrient fluid through said porous, mesh-like, open, or partially open phase-change medium.

In another preferred embodiment of the present invention the cell to be isolated or present on a filter as mentioned herein above is a rare cell. In a particularly preferred embodiment said cell is a circulating tumor cell.

In a further preferred embodiment, said optical imaging as described herein above is bright field microscopy, dark field microscopy, phase contrast microscopy, differential interference contrast microcopy, fluorescence microscopy, atomic force microscopy, confocal laser scanning microscopy or super resolution microscopy.

In a further aspect the present invention relates to processed filter material comprising isolated cells suitable for optical imaging, which is obtainable by a method according to the present invention, e.g. as defined herein above.

In another aspect the present invention relates to the use of processed filter material comprising isolated cells suitable for optical imaging, which is obtainable by a method according to the present invention, e.g. as defined herein above, for diagnostic, histological, microbiological, biochemical, oncologic, or hematologic analysis.

In yet another aspect the present invention relates to a device for processing cells to render them suitable for optical imaging, comprising:
(a) a filter material for capturing a cell as defined herein above;
(b) a layer of phase-change medium as defined herein above; and
(c) a heating and/or cooling unit.

Finally, in a specific embodiment, the present invention relates to a device for processing cells to render them suitable for optical imaging as mentioned herein above, additionally comprising a removable pressure delivery system coupled to the filter material, allowing for isolation of cells onto the filter material, and/or a means for transporting said filter material and/or said layer of phase-change medium to a carrier as mentioned herein above.

BRIEF DESCRIPTION OF THE DRAWINGS

FIG. 5 depicts an embodiment with 2 chambers separated by a filter.

DETAILED DESCRIPTION OF THE EMBODIMENTS

Figure 1:
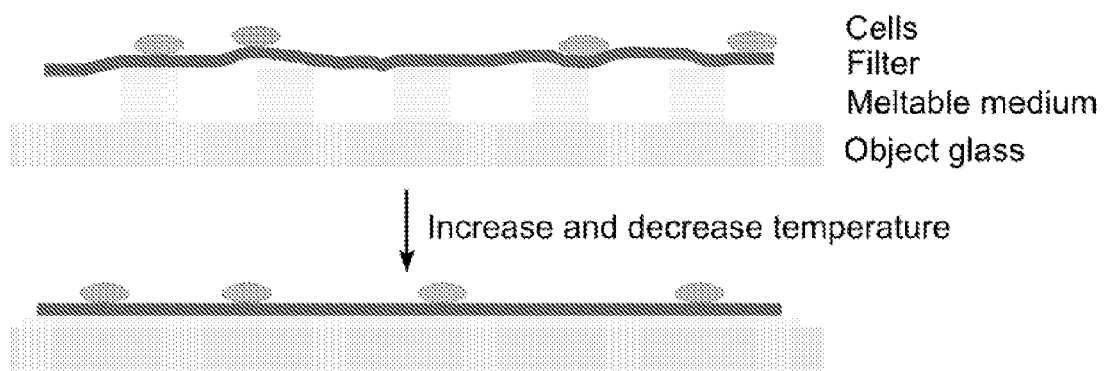
FIG. 1 depicts a cross section of the method: melting the support structure will evenly distribute the phase-changing medium between the object glass and the filter. Solidification fixes the filter in place leaving and maintaining all cells in a single optical plane and at a fixed position with respect to the object glass.

The present invention relates to means and methods for processing isolated cells to render them suitable for optical imaging.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a", "an" and "the" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)", "(i)", "(ii)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)", "(i)", "(ii)" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As has been set out above, the present invention concerns in one aspect a method for processing isolated cells to render them suitable for optical imaging, comprising the steps of (a) depositing filter material comprising captured cells on a phase-change medium; (b) melting said phase-change medium until the medium is spread out below said filter material; and (c) lowering the temperature of said phase-change medium until the medium solidifies, resulting in an optically flat filter comprising said cells at a fixed position.

The term "processing isolated cells" as used herein refers to the treatment and handling of one or more cells, which have been selected and/or enriched from their environment, i.e. to steps carried out after a selection or enrichment step of cells. A "cell" as used herein may be any type of cell, e.g. a prokaryotic cell such as a bacterial cell, or a eukaryotic cell such as a lower eukaryotic or protist cell, or a cell derived from a higher eukaryote. Typically, the cell is a cell derived from a mammalian, preferably from a human being. A cell may further be a cell derived from a domestic or farm animal, e.g. a dog, cat, cattle, swine, chicken, mouse, rat, chicken, or monkey cell.

The cell(s) may, in specific embodiments, be derived from body liquid samples such as whole blood, serum, plasma, lymph, liquor. The cell(s) may alternatively be derived from a medical or forensic sample, e.g. a biopsy sample. In further embodiments, the cells may be derived from a plant or fungus, e.g. from a callus culture. The cells may, in further embodiments, also be derived from samples such as or comprising stool, tears, saliva, nasal fluid, sputum, ear fluid, genital fluid, breast fluid, milk, colostrum, placental fluid, amniotic fluid, perspirate, synovial fluid, ascites fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid harvested from a site of an immune response, fluid harvested from a pooled collection site, bronchial lavage, or corresponding aspirates, or urine, or biopsy material, e.g. from all suitable organs, e.g. the lung, the muscle, brain, liver, skin, pancreas, stomach, etc., a nucleated cell sample, a fluid associated with a mucosal surface, hair, or skin. In addition, the cells may be derived from samples of environmental sources, e.g. water samples, meat or poultry samples, samples from sources of potential contamination etc.

The cell may accordingly be of or be derived from any known tissue type or tissue form, e.g. be derived from solid tissues, or be freely moveable or unattached. In case solid structures are given, a cell may be dissolved from such a structure, e.g. in a suitable buffer solution or nutrient solution, by employing suitable dissolution techniques as known to the person skilled in the art. In some embodiments, the cells may be directly obtained from samples. In other situations samples may be subjected to sample preparation techniques, e.g. based on standard protocols, including, for example, partial purification. For example, blood samples may be centrifuged, feces samples may be sectioned and homogenized with physiologically acceptable buffer and detergent, sputum samples may be liquefied and fractionated. Furthermore, in specific embodiments antibiotics or bactericides may be added to samples. It is preferred using isolated cells, which are not provided in a three dimensional, or optical dense more-than-one-cell layer structure or form. It is accordingly preferred using cells provided in a one-cell-layer structure or form, or a more open structure. In specific embodiments, the cells may be present singularly, i.e. as single cells without direct contact to neighbouring cells, or in conjunction, e.g. as cell agglomerations or cell pairs or cell groups. Preferably, the cells are present in a non-agglomerated conformation, more preferably as single cells not having a direct contact with neighbouring cells. In further embodiments it may be advantageous if cells are present in agglomerated confirmation, or having contact with neighbouring cells, in particular when such structures carry a biological relevance, e.g. in the case of circulating micro-emboli.

The cell(s) may have any size, form, surface, or surface-structure, e.g. comprise protein structures, or glycosylated or non-glycosylated surface entities etc. The cell(s) may accordingly have a small diameter of about 0.5 to 5 μm, or be larger, having a diameter of about 7, 8, 9, 10, 11, 12, 13, 14, 15, 16, 17, 18, 19, 20, 25 or 30 μm or more.

The cell(s) may be viable, e.g. capable of growing and/or mitotically active and/or able to divide etc.; be dormant, e.g. mitotically inactive, or unable to divide, but metabolically active; or be dead, e.g. metabolically inactive. In further embodiments, cells may be isolated as viable cells or dormant cells and die during the processing according to the present invention. In other embodiment, cells may be isolated as dead cells. In further specific embodiments, cells may be isolated as viable cells and still be viable after the processing, or parts of the processing according to the present invention.

The isolation, i.e. selection and/or enrichment of cells may be carried out according to any suitable method. For example, the cells may be filtered, e.g. passaged through a single, double or triple filter device. Alternatively, the cells may be selected or isolated according to their surface structure, e.g. by specific interactions between surface markers and corresponding ligand or binding molecules such as an antibody. In further embodiments, the cells may be selected or isolated according to form and/or size, e.g. by a cell sorting device. In yet another embodiment, the cells may be selected or isolated according to their viability, e.g. by testing their metabolic activity, or their mitotic activity. In further embodiments, the size of intracellular structures may be used for selection, e.g. the size or form of the nuclei, the presence or detectability of mitochondria, chloroplasts, vacuoles etc.

The term "suitable for optical imaging" as used herein refers to the cell's capability of being optically detectable at a high resolution and with suitable microscopy equipment, typically with a bright field microscope. Cells suitable for optical imaging are generally presented in a single optical plane, i.e. all cells within a detection area are present in a layer having a thickness of about the average diameter of the isolated cell plus about 5%, 10%, 15%, 20%, 25%, 30%, 35%, 40%, 50%, 60%, 70%, 80%, 90%, 100% or 110% of said diameter, preferably plus about 5%, 10%, 15%, 20% or 25% of said diameter. Additionally, or alternatively, a cell suitable for optical imaging may show a high contrast with respect to its surrounding. Such a high contrast may further be enhanced by staining procedures, and/or by using a diffuse light source and/or by removing interfering reflections regarding the specimen.

In a first step of the method filter material comprising captured cells as defined herein above is deposited on a phase-change medium. The term "filter material" as used herein refers to any material which is capable of bearing or sustain one or more cells, preferably a group of more than 10, 50, 100, 500, 1000, 5000 or 10000 cells. The material may be porous or have openings allowing the penetration of water molecules or other liquid molecules. The material may further be capable of allowing the penetration of air or oxygen molecules. In certain embodiments, a filter material may additionally have a filtration or retention function, e.g. by providing pores or pore-like structures allowing the passing of certain cells, cell types, cell sizes etc, while retaining other cells, cell types or cell sizes. Filter material having a filtration or retention function may accordingly have any suitable pore size, pore arrangement, thickness, and/or be composed of any suitable material known to the person skilled in the art. The filter material may have any suitable form, for example be circular, ellipsoid, rectangular, quadratic, triangular, or have a mixture of the mentioned forms. Preferred are circular filter materials. In further embodiments, the filter material may covering a continuous, closed interior area, or it alternatively be of a ring form with a central or asymmetric hole within the interior area, or comprise two or more openings within the interior area.

A "phase-change medium" as used herein refers to a medium which shows a phase transition between a solid phase and a liquid phase within a temperature range suitable for the processing of living entities, preferably within a temperature range of about 25° C. to 70° C. Preferably, a phase-change medium solidifies at temperatures above room temperature, e.g. at a temperature higher than 28° C. The phase transition may typically be induced by the addition of energy to the medium. For example, by using UV radiation, infra red radiation or direct heating, a phase transition may be induced, i.e. the medium becomes fluidic, preferably viscous. Furthermore, a phase-change medium as used in the context of the present invention should further have the property of being translucent in the solid phase. The term "translucent" as used herein refers to the capability of letting pass about 50%, 60%, 70%, 80%, 85%, 90%, 95%, 96%, 97%, 98%, 99% or 100% of an applied light beam. In addition, or alternatively, the phase-change medium may be diffuse. The term "diffuse" as used herein refers to the phase-change medium's capability to function as a diffuser of visible light. Accordingly, the medium may advantageously—in addition to presenting cells in a single optical plane—effectively remove reflections between the filter material, the support material and the optical imaging equipment, in particular one or both sides of the microscope slide. These properties of the phase-change medium thus contribute to the overall image quality.

In further embodiments of the present invention the phase-change medium may have a thickness of about 10 to 100 µm, e.g. a thickness of 10 µm, 15 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm or more, or any value in between the mentioned values. The thickness may, in specific embodiments, also be less. In a particularly preferred embodiment, the phase-change medium has thickness of about 40 µm. It is particularly preferred to adjust the thickness of the phase-change medium such that the no liquid phase-change medium comes up through the pores or openings of the filter material. In other embodiments of the present invention, the phase-change medium may cover an area of about 10%, 20%, 30%, 40%, 50%, 60%, 70%, 80%, 90%, 100%, 110% or more or any percentage in between these values of the area of a filter material as mentioned above.

Figure 5A:
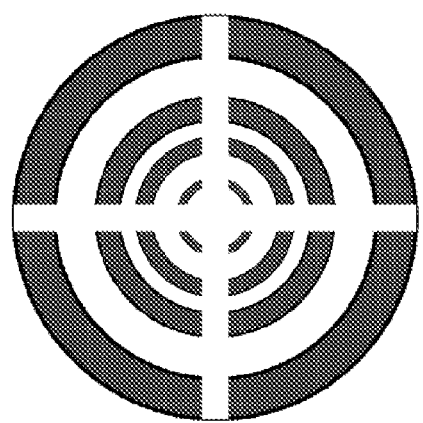
FIG. 5A shows a meltable support structure in top view.

In preferred embodiments, the phase-change medium may initially be in a solid transition state. In a solid transition state the phase-change medium may have any suitable form, for example be circular, ellipsoid, rectangular, quadratic, triangular, or have a mixture of the mentioned forms. Preferred are circular phase-change media. In further embodiments, the phase-change medium may be covering a continuous, closed interior area, or it may alternatively have a ring form with a central or asymmetric hole within the interior area, or comprise two, three, 4, 5, 6, 7, 8 or more openings within the interior area. An example of the form of a phase-change medium envisaged by the present invention is depicted in FIG. 5A.

It is preferred that the phase-change medium be adjusted to the size, area or diameter of the filter material, e.g. by having the same, essentially the same or a similar form, size, area or diameter as the filter material. In further embodiments, the phase-change medium may be adjusted to the size, area or diameter of the filter material such that said phase-change medium in a liquid transition state covers the same, essentially the same or a similar area and/or has the same or essentially the same or a similar form, size or diameter as the filter material in order to enhance the spreading of the phase-change medium under the filter material and/or in order to reduce the time at higher temperature needed to establish a flat surface.

In other embodiments, the phase-change medium may have the same, essentially the same or a similar form as the filter material, e.g. if the filter material is circle, the phase-change medium is also circular, if the filter material is of a rectangular form, the phase-change medium may also be rectangular etc. In further embodiments, the phase-change medium may have a different form than the filter material. Preferably, the phase-change medium may have a smaller size than the filter material. In preferred embodiments, the phase-change medium may have a ring-like form, with the filter material having a circular form. Alternatively, the phase-change medium may have a grate- or mesh-like structure, with the filter material having a rectangular form etc.

The term "depositing filter material on a phase-change medium" as used herein means that a filter material as defined herein above, in particular a filter material comprising cells or captured cells, is transferred from the site of filtration or capturing one or more cells to a site where a phase-change medium is located, preferably, where a phase-change medium can be treated such that a transition from a solid to a liquid phase can take place. The filter material is typically provided on top of the phase-change medium. The filter material may, in specific embodiments, cover the underlying phase-change medium. In certain embodiments and situations, the phase-change material may be placed or be present also on top of the filter material. In further specific embodiments, the phase-change material may be located in a rim or ring form around a filter material, or be only partially located beneath a filter material. In further embodiments, the phase-change medium may be positioned partially below and on top of the filter material. In yet another embodiment, a filter material may be positioned between two layers of phase-change medium in a sandwich like manner, i.e. one layer beneath the filter material, another layer on top of the filter material. If the phase-change medium is used on top of the filter material, or on both sides, it is preferred to have a thin, or very thin layer of phase-change medium, e.g. not exceeding the maximal thickness of a captured cell, or 50%, 40%, 30%, 20%, 10% of the maximal thickness of a captured cell.

Figure 4:
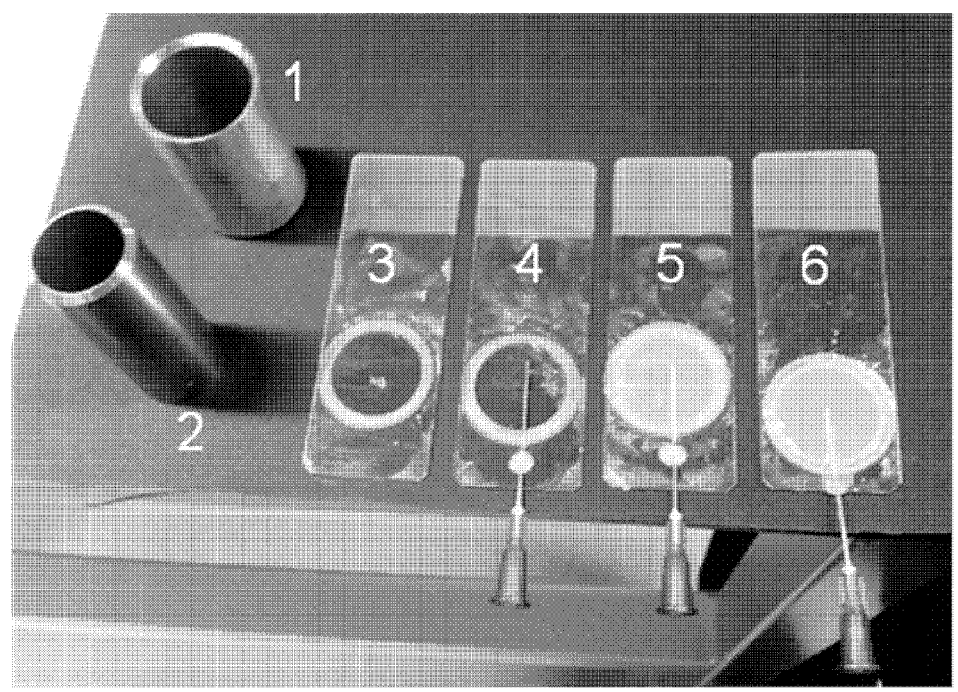
FIG. 4 shows the steps towards creation of a simple prototype of a device to test the integrated functionality of filtering and optically flattening of a filter.
Figure 5B:
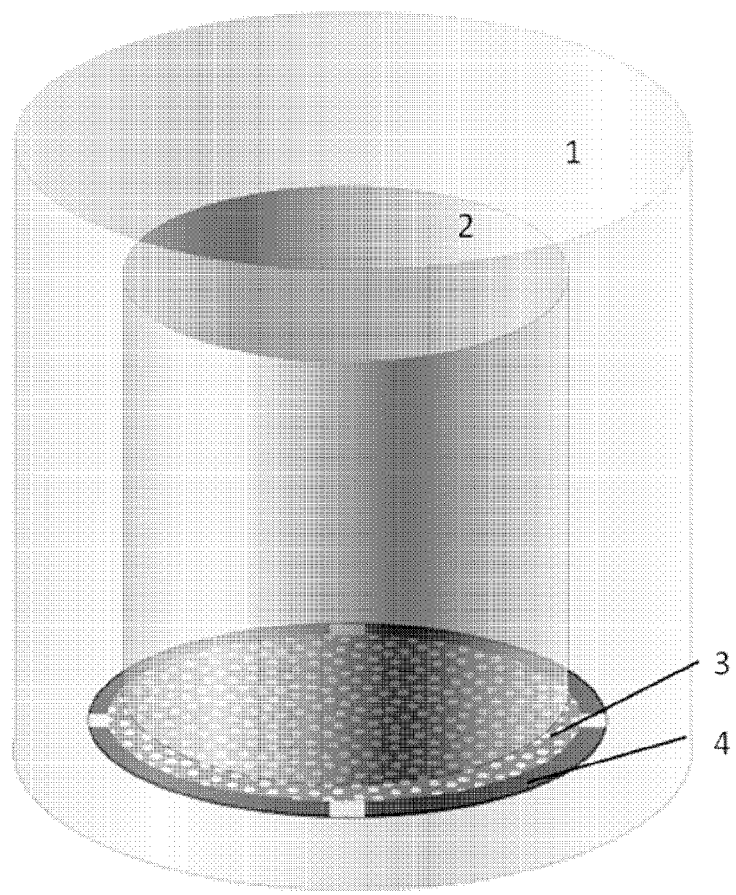
FIG. 5B shows a possible support structure (4, FIG. 5A) supporting the filter. The first compartment is sealed by the inner tube (2) and the filter (on top of the support structure), the second compartment is sealed by the inner (2) and outer tube (3). In this embodiment, the cell supply and vacuum generating machinery can be removed easily, after which the filter (3) may be flattened and imaged.

The depositing procedure may in certain embodiments be integrated within a device structure or an overall processing workflow. Examples are a depositing step lined to the removal of device units necessary for filtration or cell capturing processes, and/or linked to the removal of liquid residuals form a filter material. In these embodiments, a phase-change medium may already have been present in an initial phase, e.g. during a filtration process or a cell capturing process, or the phase-change medium may take the position of previously used structures for carrying out filtration or cell capturing processes. In preferred embodiments, an overall processing workflow may include the use of compartment structures as shown in FIG. 5B, or the use of entities as shown in FIG. 4.

In a second step of the method the phase-change medium as defined herein is melted until the medium is spread out below the filter material as defined herein. The melting step may be carried out in accordance with the type, size, thickness of the phase-change medium, its temperature properties, the covered area, the room temperature or any other suitable parameter. The melting temperature may be set to a high value within a suitable temperature range as indicated herein, e.g. of about 37° C. to 70° C. in order to enhance the velocity of the phase transition. In such an embodiment, the viability of the cells may not be of importance, e.g. due to a subsequent fixation or chemical treatment etc. In other embodiments, the melting temperature may be set to a lower value, e.g. a value of not more than 37-50° C., preferably not more than 37° C. In this embodiment, cells may be viable after the melting procedure and may subsequently be tested with specific test for living cells. Alternatively, such cells may be kept alive on the filter material, e.g. by providing suitable nutrients etc. The melting period may also be adapted to the type, size, thickness of the phase-change medium, its temperature properties, the covered area, the room temperature or any other suitable parameter. The melting period may, for instance, be a period of 1 sec, 5 sec, 7 sec, 10 sec, 15 sec, 20 sec, 25 sec, 30 sec, 35 sec, 40 sec, 45 sec, 50 sec, 1 min, 2 min, 3 min, 4 min, 5 min, 7 min, 10 min, 15 min or more, or any value in between the indicated values.

The melting of the phase-change medium may be conveyed by any suitable energy transfer unit, e.g. by a heating device, a source of UV light, an infrared light source, a microwave source etc. An energy transfer unit according to the present invention may, in specific embodiments, be located in the vicinity of the filter material, or within a device or apparatus structure. A preferred energy source is a Peltier element.

In specific embodiments of the present invention, a melted phase-change medium may be provided from the outside, e.g. in the form of a syringe or via fluid connection to the filter material. In these embodiments, a depositing step as mentioned above is not necessary, since the temperature increasing activity is carried out at a certain distance to the filter material. The melted phase-change medium may further be transported to the filter material with the help of valves, pumping units, tubing entities or any other micro fluidic transportation means. In specific embodiments, the transport process may be integrated within the workflow of a micro fluidic device or apparatus.

The term "phase-change medium spread out below the filter material" as used herein refers to a complete or essentially complete dispersion of the phase-change medium in the entire area of the filter material. It is preferred that the spreading or dispersion of the phase-change medium leads to an equiplanar layer of medium of essentially the same thickness and density in all areas of the filter material. The spread out phase-change medium may preferably be free, or be essentially free of air bubbles.

In further, alternative embodiments of the invention, the dispersion or spread out of the phase-change medium may also be localized to specific zones of the filter material, e.g. the centre of the filter material, distal zones of the filter material, zones wherein cells are located on a filter material, e.g. in scenarios in which only very few cells are present on a filter material, or any other zone of the filter material. The zones may, in further embodiments, be predetermined, e.g. by the provision of filter structures channelling the melted phase-change medium.

In further specific embodiments of the present invention, a melting step as defined herein may be repeated one or more times, e.g. in case the phase-change medium has not spread out completely in the entire area of the filter material, or in case the layer of medium may not be of essentially the same thickness.

In a third step of the method the temperature is lowered until the phase-change medium solidifies. The temperature lowering step may be carried out in accordance with the degree of melting and/or spreading of the phase-change medium, its temperature properties, the covered area, the room temperature or any other suitable parameter. The final temperature which may reached by the temperature lowering activity may be set to a suitable temperature range as indicated herein, e.g. of about 4° C.-35° C. The final temperature may preferably be set to a low temperature of about 4, 8, 10, 20, 22, 24, 25 or 26° C. in order to enhance the velocity of the phase transition towards the solid phase of the phase-change medium. The lowering of the temperature may be carried out by an active cooling process, e.g. by cooling the melted medium to the indicated temperature, or by terminating the heating or melting process, e.g. by switching off heating, UV-light or infrared light, or microwave devices and letting the phase-change medium adapt its temperature to the surrounding temperature, or the room temperature.

In further embodiments, the temperature lowing step may be carried out in cascades, e.g. by lowering the temperature in 5° C., 10° C., 15° C., or 20° C. leaps, or by a direct lowering, i.e. cooling to the final temperature. Further lowering pattern or temperature decrease programs would be known to the person skilled in the art and are also envisaged by the present invention.

In certain, specific embodiments of the present invention a cascading lowering of the temperature may be combined with partial temperature increases. E.g. after a lowering of the temperature for 10° C., an increase of 5° C. may be performed, followed by a further decrease of the temperature etc.

The phase-change medium may be considered as being solidified when comprising no or essentially no liquid sections or areas.

The lowering of the temperature of the phase-change medium may be conveyed by any suitable cooling device. Such a cooling device may, in specific embodiments, be located in the vicinity of the filter material, or within a device or apparatus structure. A preferred cooling device is a Peltier element. In further preferred embodiments, the Peltier element may be used for the melding step as well as the subsequent cooling step. Furthermore, the Peltier element may be instructed to perform specific melting and cooling programs as known to the person skilled in the art.

The temperature lowering step of the phase-change medium may be carried out such that the filter material is converted to an optically flat filter, preferably a filter comprising cells presented in a single optical plane, i.e. all cells within a detection area are present in a layer having a thickness of about the average diameter of the isolated cell plus about 5%, 10%, 15%, 20%, 25%, 30%, 35%, 40%, 50%, 60%, 70%, 80%, 90%, 100% or 110% of said diameter, preferably plus about 5%, 10%, 15%, 20% or 25% of said diameter.

In further preferred embodiments, the cells may be at a fixed position on the filter due to their embedding in the phase-change medium. This fixed position may be detected and memorized in order to allow for subsequent analysis steps, e.g. after a first round of molecular analysis of the processed filters in a microscope etc. Thus, open the identification and selection of specific cells via microscopic analysis, the fixed position allows for a subsequent removal or tagging of the identified cells, e.g. for further individual tests.

In a preferred embodiment of the present invention the method as defined above additionally comprising the initial step of capturing a cell on a filter material. The "capturing" of one or more cells on a filter may be performed by any suitable means resulting in the presence of (a) cell(s) on a filter material as defined herein above or below. In one embodiment, the capturing may be carried out by a filtration process, e.g. via the employment of a pressure delivery system, or the use of fluid flows, e.g. in a fluidic or microfluidic system or device. In further embodiments, the capturing of a cell on a filter material may be performed by selecting or isolating the cells according to their surface structure, e.g. by specific interactions between surface markers and corresponding ligand or binding molecules such as an antibody. Preferred are adhesion techniques based on, e.g. epithelial adhesion molecule (EpCAM). Different implementations of these techniques, which are envisaged by the present invention, would be known to the skilled person. One preferred embodiment is an immuno-magnetically selection process, e.g. based on ferrofluidic nanoparticles. In a further embodiment, the cells may be captured subsequent to enrichment and/or culturing steps. Furthermore, the cells may be enriched or specifically processed in order to remove a potential excess of immuno-magnetic particles prior to imaging.

In specific embodiments, the capturing of cells of different sizes, of specific origins, or of specific surface constitutions etc. may be implemented by using filter material or filter sets excluding different sizes or forms of cells. For example, in order to capture small cells such as bacterial cells, a one or a two or three filter set may be used. In case environmental samples are tested, it may be advantageous using a one filter set with an appropriate pore size. In case blood or other body liquids are used, it may be advantageous using a two or more than two filter setup wherein one filter captures large, e.g. human cells, whereas a second filter with smaller pores captures bacterial cells. Further details may b derived from suitable publications, e.g. from Sage and Neece, 1984, J Clin Microbiol., 20(1): 5-8.

In a preferred embodiment the filter material may be capable of size excluding cells to be isolated from the environment, e.g. form a fluid or solution, typically from a blood sample. The size exclusion may be implemented by specific pore or opening sizes of the filter material. In addition, the pore form, being cylindrical, circular, ellipsoid, rectangular, or rhombic. A further relevant parameter is the flow velocity or fluidic pressure during filtration or capturing processes. The flow velocity may, for example, range from 50 ml to 0.1 ml per minute. However, the present invention also envisages further flow velocities below or above the indicated range. In addition, the 3-dimensional pore form may be modified in order to achieve specific size and/or flexibility exclusions. In specific embodiments it is preferred to use filter material allowing for preservation of the cell membrane integrity of cells, i.e. to capture intact cells and/or viable cells. In alternative embodiments, filter material may be used which does not necessarily preserve the cell membrane integrity. The filter material and optionally the filtration procedure or the filtration parameters may accordingly be adapted to the size of cells, which are supposed to be captured, and/or the functional requirements for the captured cells, i.e. being intact or viable etc.

In preferred embodiments of the present invention, the filter material may have a pore size of about 0.5 to 20 μm, e.g. a pore size of about 0.5 μm, 0.75 μm, 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm or 20 μm or more, or any value in between the indicated values. The pore size may be selected according to the cell to be isolated. In further specific embodiments of the present invention, the filter material or the filter material implemented within a filtration procedure may have a size exclusion of about 0.5 to 20 μm, e.g. a size exclusion of 0.5 μm, 0.75 μm, 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm or 20 μm or more, or any value in between the indicated values. The term "size exclusion" as used herein means that at a value of e.g. 5 μm cells having an averaged diameter of about 5 μm and larger are captured on the filter material, whereas cells having an averaged diameter of less than 5 μm pass the filter and are not captured.

For the capturing of bacterial cells, it is preferred to use filter material of a pore size of about 0.5 μm to 4 μm. For the capturing of blood components without platelets, it is preferred to use filter material of a pore size of about 4 to 10 μm. For the capturing of blood components without red blood cells, it is preferred to use filter material of a pore size of about 7 to 12 μm. For the capturing of tumor cells a larger pore size of about 8 to 20 μm may be used. It is particularly preferred to use a pore size of 8 μm, which is considered as adequate pore size for the isolation of tumor cells, in particular for the isolation of epithelia tumor cells. In further specific embodiments, also viral particles, viruses or bacteriophages may be captured or isolated from a sample, e.g. from a suspension of lysed host cells. For such capturing procedure a pore size of about 20 nm to 300 nm, more preferably of about 20 nm to about 50 nm may be used. Corresponding filters may be size-exclusion/removal-of-virus-filters such as Ultipor filters marketed by Pall Corporation. If viruses, viral particles or bacteriophages are to be captured or isolated, the filters are preferably combined with pre-filters of a larger pore size. It is an advantage of the present invention that for example AFM and/or STM investigations of virus particles benefit greatly from the uniform, very flat surface that is created by the methods according to the present invention.

In a preferred embodiment the filter material to be used is composed of a material, which is resilient, and/or resistant to fluid pressure and/or chemically inert, i.e. not reacting with biological or biochemical components within sample and/or resistant to temperature changes, e.g. within the range of about −80° C. to +130° C. Furthermore, the filter material may be resistant to UV radiation.

In preferred embodiments, the filter material may be a suitable polymer material. Preferred examples of a polymer material are polycarbonate, nylon or parylene. Also envisaged are similar materials, or derivatives or combinations thereof, e.g. in case a two or more layer filter is used. In further preferred embodiments, the filter material may be a suitable non-polymer material. A preferred example of a non-polymer material is silicon. Also envisaged are similar materials, or derivatives or combinations of polymer and non-polymer material, e.g. in case a two or more layer filter is used. In further preferred embodiments of the present invention, the filter material may be 3D microfilter composed of parylene sections arranged in a 3 dimensional manner comprising a bollard like structure below the pore opening, e.g. as derivable from Zheng et al., 2011, Biomed Microdevices, 13: 203-213. In a particularly preferred embodiment of the present invention, the filter material is a polycarbonate filter, more preferably a Whatman Cyclopore track etched membrane-filter, even more preferably a Whatman Cyclopore track etched membrane-filter with 8 μm pores.

In a further preferred embodiment of the present invention, the phase-change medium as defined herein above is a medium which melts and/or solidifies in a temperature range of about 25° C. to 70° C. For example, the phase-change medium may melt at a temperature of about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70° C. or at any temperature in between these values. Furthermore, the phase-change medium may solidify at a temperature of about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70° C. at any temperature in between these values. The term "melts" as used herein refer to the phase-change medium's capability of completely or essentially completely transiting from a solid phase to a liquid phase. The term "solidifies" as used herein refers to the phase-change medium's capability of completely or essentially completely transiting from a liquid phase to a solid phase. It is noted, that for the same phase-change medium, i.e. a phase-change medium having a clear defined molecular composition, e.g. a paraffin wax, its physical phase transition properties are identical. Thus, for such a phase-change medium the melting temperature of that medium is identical to its solidification temperature. However, the present invention encompasses the employment of different phase-change media, which may be selected from media having the above indicated range of melting and solidification temperatures.

In further preferred embodiments of the present invention the phase-change medium comprises a porous, mesh-like, open, or partially open structure. The phase-change medium may, for example, have a 3-dimensional structure of a certain thickness allowing the presence of openings or cavities. In preferred embodiments, such openings may have the form of a channel, a passage or a pipe element. These structures may be able to provide a connectivity between all sectors or areas of a phase-change medium, e.g. a connectivity for a fluid and/or for gaseous entities, e.g. for air. Preferably, such structures or elements allow the passage of a fluid through the cavities of the phase-change medium.

Cavities, openings or channel structures may, for example, be provided by carving out or cutting out corresponding sectors from a compact mass of the phase-change medium. Alternatively, the phase-change medium may be casted as melted or liquid material into a corresponding mold and subsequently be solidified, followed by the extraction of the mold. Alternatively, a laser or laser device may be used to cut out a structure by either locally melting or burning the material away in specified places.

In case a filter material is placed on said phase-change medium, or connected therewith, the porous, mesh-like, open or partially open structure of the phase-change medium, and/or the presence of channel, passage or pipe elements may be used for the delivery of fluids or solutions, e.g. nutrient solutions to cells captured on said filter material. By using the connectivity features of the phase-change medium, a culturing of captured cells, in particular viable captured cells, on a filter material as described herein becomes possible. Thus, captured cells may be kept alive, provided with inducing or inhibiting factors, selected nutrients etc. during a time period of about 30 min to several weeks. Furthermore, cells may, after culturing, be removed from the filter, e.g. by using standard cell culturing methods such as trypsinization, and subsequently be transferred to standard cell culture flasks. The captured cells may be analysed via optical imaging procedures, or be processed etc. as described herein. Typically, the porous, mesh-like, open, or partially open structure of the phase-change medium may be present in a solidified state, e.g. after the depositing of a filter material on the phase-change medium, i.e. before any melting step. Subsequent to the melting step as defined herein, the phase-change medium may have lost its porous, mesh-like, open, or partially open structure, and have transformed into an optically flat filter. In specific embodiments, the phase-change medium may however still comprise a porous, mesh-like structure, or at least partially open structure after having been melted and solidified. For example, in specific areas such a structure may be present, while other areas show an optically flat structure.

In preferred embodiments of the present invention the phase-change medium as described herein is a hydrocarbon wax. The term "hydrocarbon wax" refers to a hydrocarbon or mixture of hydrocarbons of the formula $C_nH_{2n+2}$ with n=20 to 40 or mixtures of these hydrocarbons with further molecules, preferably further organic molecules. The hydrocarbon wax may, for example, be composed of a mixture of saturated n- and isoalkanes, and/or naphthenes, and/or alkyl- and naphthene-substituted aromatic compounds and/or cycloalkanes. The alkanes or other molecules comprised in the hydrocarbon wax may be branched or unbranched, or comprise a mixture of branched and unbranched molecules. Branched molecules may have different degrees of branching, or have different degrees of branching, e.g. comprise 1, 2, 3 or more branches, or be further branched within a branch, i.e. having 1, 2, 3 or more $2^{nd}$ generation branches. In a preferred embodiment, the phase-change medium is a paraffin wax. A "paraffin wax" max comprise hydrocarbons or mixture of hydrocarbons of the formula $C_nH_{2n+2}$ with n=20 to 40. Further envisaged and potentially useful examples of phase-change medium include molecules having the molecular formula $C_nH_{2n+2}$ with n=24 to 36, or with n=24, $C_nH_{2n+2}$ with n=25, $C_nH_{2n+2}$ with n=26, $C_nH_{2n+2}$ with n=27, $C_nH_{2n+2}$ with n=28, $C_nH_{2n+2}$ with n=29, $C_nH_{2n+2}$ with n=30, $C_nH_{2n+2}$ with n=31, $C_nH_{2n+2}$ with n=32, $C_nH_{2n+2}$ with n=33, $C_nH_{2n+2}$ with n=34, $C_nH_{2n+2}$ with n=35, $C_nH_{2n+2}$ with n=36, $C_nH_{2n+2}$ with n=37, $C_nH_{2n+2}$ with n=38, $C_nH_{2n+2}$ with n=39, $C_nH_{2n+2}$ with n=40, $C_nH_{2n+2}$ with n=41, $C_nH_{2n+2}$ with n=42, $C_nH_{2n+2}$ with n=43, $C_nH_{2n+2}$ with n=44, or $C_nH_{2n+2}$ with n=45, or any mixture of these molecules. Such mixtures may be present in any suitable proportion, comprising 2, 3, 4, 5,6 7, 8, 9, 10 or more molecules, with comprising one molecule in an amount of 5%, 10%, 15%, 20%, 30%, 40%, 50%, 60%, 70%,80% or 90% and comprising a second or further molecule in a corresponding amount.

In another preferred embodiment the phase-change medium is a disordered material that has uniform optical scattering properties. Envisaged examples of this material group are $C_{10}$ to $C_{20}$ organic acids, e.g. capric acid to arachidic acid. The group may also include esters and alcohols with varying carbon chain lengths. The phase-change medium may, in other embodiments, be composed of reversible systems based on the Diels-Alder mechanism.

In further specific embodiments of the present invention the phase-change medium may be an animal wax or vegetable wax. Typically, waxes are biosynthesized by several plants or animals and may comprise wax esters, wax acids, wax alcohols, and hydrocarbons. Wax esters may be derived from a variety of carboxylic acids and a variety of fatty alcohols. The composition of the animal wax may depend on species and on the geographic location of the organism. Examples of animal waxes include beeswax, or other insect secreted waxes, as well as sperm whale wax. Examples of vegetable waxes include Carnauba wax which is derived the Brazilian palm, as well as candelilla wax, ouricury wax, sugarcane wax or retamo wax. Vegetable waxes may preferably be epicuticular waxes of plants comprising mixtures of substituted long-chain aliphatic hydrocarbons, or contain alkanes, fatty acids, primary and secondary alcohols, diols, ketones,and/or aldehydes. In further preferred embodiments of the present invention the phase-change medium may be mounted on a carrier.

The term "carrier" as used herein refers to any structure allowing to support the phase-change medium. The carrier should preferably be resistant to temperatures used for the melting/solidification procedure as defined herein. In addition, or alternatively, the carrier may be translucent, e.g. as defined herein above in the context of the phase-change medium. Thus, the carrier may, for example, be translucent for the spectrum of the sun light, and/or for specific wavelength ranges within the spectrum of the wavelengths of the sun light or outside of the spectrum of the wavelengths of the sun light. Examples of such wavelengths include the wavelengths of the ultraviolet light. Thereby, an optical imaging of captured cells on the filter material may become feasible.

Preferred carriers are glass carriers. Also preferred are carriers composed of polymer or plastic material, e.g. of thermoplastic or elastomeric material. The term "thermoplastic" as used herein refers to a thermosoftening plastic polymer, which becomes liquid when heated and freezes to a glassy state when cooled sufficiently. The thermoplastic may be a high-molecular-weight polymer whose chains associate through weak Van der Waals forces, stronger dipole-dipole interactions and hydrogen bonding; or stacking of aromatic rings. Examples of thermoplastics include Acrylonitrile butadiene styrene (ABS) Acrylic (PMMA), Celluloid, Cellulose acetate, Cycloolefin Copolymer (COC), Ethylene-Vinyl Acetate (EVA), Ethylene vinyl alcohol (EVOH), Fluoroplastics (PTFE, with FEP, PFA, CTFE, ECTFE, ETFE), Ionomers, acrylic/PVC alloy, Liquid Crystal Polymer (LCP), Polyacetal (POM or Acetal), Polyacrylates (Acrylic), Polyacrylonitrile (PAN or Acrylonitrile), Polyamide (PA), Polyamide-imide (PAI), Polyaryletherketone (PAEK or Ketone), Polybutadiene (PBD), Polybutylene (PB), Polybutylene terephthalate (PBT), Polycaprolactone (PCL), Polychlorotrifluoroethylene (PCTFE), Polyethylene terephthalate (PET), Polycyclohexylene dimethylene terephthalate (PCT), Polycarbonate (PC), Polyhydroxyalkanoates (PHAs), Polyketone (PK), Polyester, Polyethylene (PE), Polyetheretherketone (PEEK), Polyetherketoneketone (PEKK), Polyetherimide (PEI), Polyethersulfone (PES), Polyethylenechlorinates (PEC), Polyimide (PI), Polylactic acid (PLA), Polymethylpentene (PMP), Polyphenylene oxide (PPO), Polyphenylene sulfide (PPS), Polyphthalamide (PPA), Polypropylene (PP), Polystyrene (PS), Polysulfone (PSU), Polytrimethylene terephthalate (PTT), Polyurethane (PU), Polyvinyl acetate (PVA), Polyvinyl chloride (PVC), Polyvinylidene chloride (PVDC), and Styrene-acrylonitrile (SAN). The term "elastomeric material" as used herein refers to a polymer with the property of viscoelasticity, wherein the monomers, which link to form the polymer are typically made of carbon, hydrogen, oxygen and/or silicon. Elastomeric materials may be amorphous polymers existing above their glass transition temperature, so that considerable segmental motion is possible. At ambient temperatures they may be relatively soft and deformable. Examples of elastomeric material include Synthetic polyisoprene (IR), Polybutadiene (BR), Styrene-butadiene Rubber (copolymer of polystyrene and polybutadiene, SBR), Nitrile rubber (copolymer of polybutadiene and acrylonitrile, NBR), Hydrogenated Nitrile Rubbers (HNBR), Chloroprene rubber (CR), polychloroprene, Neoprene, EPM (ethylene propylene rubber, a copolymer of ethylene and propylene), Epichlorohydrin rubber (ECO), Polyacrylic rubber (ACM, ABR), Silicone rubber (SI, Q, VMQ), Fluorosilicone Rubber (FVMQ), Fluoroelastomers (FKM, and FEPM) Viton, Tecnoflon, Fluorel, Aflas, Perfluoroelastomers (FFKM) Tecnoflon PFR, Kalrez, Chemraz, Perlast, Polyether block amides (PEBA), Chlorosulfonated polyethylene (CSM), Ethylene-vinyl acetate (EVA), Thermoplastic elastomers (TPE), Elastron, Thermoplastic olefins (TPO), resilin, elastin and Polysulfide rubber.

In a specific embodiment the carrier may be composed of an organic polymer selected from the group of polyethylene, polypropylene, polystyrene, polycarbonate and polycycloolefin. "Polyethylene" as used herein refers to a polymeric material composed of long chains of the monomer ethylene. Polyethylene material may be present in different forms of density and/or branching. Examples of polyethylene material include Ultra high molecular weight polyethylene (UHMWPE), Ultra low molecular weight polyethylene (ULMWPE or PE-WAX); High molecular weight polyethylene (HMWPE); High density polyethylene (HDPE); High density cross-linked polyethylene (HDXLPE); Cross-linked polyethylene (PEX or XLPE); Medium density polyethylene (MDPE); Linear low density polyethylene (LLDPE); Low density polyethylene (LDPE) and Very low density polyethylene (VLDPE). "Polypropylene" as used herein refers to a thermoplastic polymer composed of monomeric propylene units. Examples of polypropylene include homopolymer polypropylene, random copolymer polypropylene, and block copolymer polypropylene. Propylene may also comprise polypropylene derivatives comprising units of polypropylene and ethylene or polyethylene units. "Polystyrene" as used herein refers is an aromatic polymer made from the aromatic monomer styrene. Examples of polystyrene include isotactic polystyrene, atactic polystyrene and syndiotactic polystyrene. "Polycarbonate" as used herein refers to thermoplastic polymers comprising carbonate groups. Polycarbonates may be derived from a combination of bisphenol A and phosgene, a transestrification of bisphenol A and diphenyl carbonate. Polycarbonate material may in one embodiment be transparent."Polycycloolefine" as used herein refers to of alkene hydrocarbons which contain more than one closed ring of carbon atoms, but have no aromatic character. Polycycloolefines may, for example, be composed of monomeric alkenes such as cyclopropene, cyclobutene, cyclopentene, cyclohexene, cycloheptene, 1,3-cyclohexadiene, 1,4-cyclohexadiene or 1,5-cyclooctadiene. In further embodiments, the carrier may be comprised of material suitable for the production of optical instruments, e.g. lenses, eyeglasses, sunglasses, contact lenses etc. Examples of such material are materials with a high refraction index, e.g. plastic materials with a high refraction index. The group of plastic materials suitable for the production of optical instruments comprises, for example, polycarbonate plastics such as polyallyldiglycolcarbonat (PADC) or CR-39 or derivatives thereof.

In a typical embodiment, the carrier is a glass slide as used for standard microscopes.

In further embodiments of the present invention, the carrier as defined herein above may comprise or may additionally comprise a position marker. The term "position marker" as used herein refers to a marking, grid, system of lines, dimension or length indication, number or letter code, barcode, matrix code or any other suitable sing known to the person skilled in the art, allowing to determine the location of a cell, its size or diameter, the distance to a neighbouring cell etc. In specific embodiments, the position marker may be a position marker detectable upon induction under specific wavelengths. For example, the position marker may be detectable when excited with light of a wavelength of about 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, or higher. Other, physical markers may be present to facilitate AFM of STM microscopy.

In a further, preferred embodiment of the present invention the method for processing isolated cells as described herein comprises as additional step an activity to be carried out on the isolated cells. Such an activity may be performed on cells captured on a filter material before the phase-change medium has been melted and solidified, or it may be preformed after the melting and solidification of the phase-change medium. The activity may accordingly be carried out in situ, e.g. within a device according to the present invention, or it may b performed at a different site, e.g. in a specific laboratory, a different device etc. The activities may accordingly be adapted to the specific situations, e.g. the presence of phase-change medium or its absence, the presence of additional entities such as carriers. Further envisaged is an automatization or semi-automatization of the activities, e.g. in a microfluidic system or environment. For example, activity steps may be carried out by roboters, or by a system comprising mechanically moveable parts controlled by a computerized control unit.

The activity may, in one embodiment, be a fixation activity. "Fixation" as used herein is understood as a preparation step for a subsequent staining and may depend on the type of analysis planned. Typically, fixation aims to preserve the shape of the cells as much as possible. Fixation may, in certain embodiments, be heat fixation which used to kill, adhere, and alter the cells in order to allow the cells accepting stains. Alternatively, the cells may be fixated by air drying. In a further alternative, a chemical fixation may be performed. Envisaged examples of chemical fixation are the use of formaldehyde, ethanol, methanol and/or picric acid. In further embodiments, fixation may be followed by antigen retrieval techniques such as brief heating of short exposure(s) to microwave radiation.

The activity may, in a further embodiment, be a staining activity. "Staining" as used herein refers to the addition of class-specific (e.g. DNA, protein, lipid, carbohydrate specific) dye to a cell or cell comprising filter material to qualify and/or quantify the presence of said class of compounds. The term also includes fluorescent tagging, e.g. with fluorescent labels or markers. The staining may be carried out in vivo, i.e. with living cells, preferably with cells being cultured in situ on the filter material as described herein, or with living cells captured on the filter material as described herein. In a typical embodiment, the staining is carried out with cells being fixated as defined herein above. The staining procedure may be adapted to the cell type present on the filter material. For example, bacterial cells may be stained according to a Gram staining procedure, or by a Ziehl-Neelsen staining Further envisaged staining procedures include haematoxylin and eosin staining, Pap staining, PAS staining, Masson's trichrome staining, Romanovsky staining, Silver staining or Conklin staining Further envisaged staining approaches include staining with acridine orange, Bismarck brown, carmine, Coomassie blue, crystal violet, DAPI, eosin, ethidium bromide, acid fuchsine, Hoechst stains, iodine, malachite green, methyl green, neutral red, Nile blue, Nile red, osmium tetroxide, rhodamine, or safranin. Staining may also include fluorescent tagging or molecular tagging, e.g. by using fluorescent labels or markers and/or antibodies being fluorescently tagged or be recognized by secondary antibodies being tagged or recognizable. This can, for example, be accomplished using suitable labels, which can be conjugated to a detection molecule able to recognize structures or entities on the surface or in the cells captured on filter material according to the present invention. Examples of suitable labels include fluorescent dyes (e.g. fluorescein, rhodamine, phycoerythrin, fluorescamine), chromophoric dyes (e.g. rhodopsin), chemiluminescent compounds (e.g. luminal, imidazole) and bioluminescent proteins (e.g. luciferin, luciferase, green fluorescent protein, yellow fluorescent protein, derivatives thereof). A detection molecule such as an antibody may further be labeled with a fluorescent label like FITC, 6-FAM, HEX, TET, ROX, Cy3, Cy5, Texas Red and/or at the same time with a quenching label like TAMRA, Dabcyl, Black Hole Quencher, BHQ-1 or BHQ-2. Detection molecules may also preferably be labeled with enzymes or enzymatic domains generating a luminescent, a fluorescent or an electrochemical signal. Particularly preferred examples of such enzymes include horseradish peroxidase, alkaline phosphatase and beta-lactamase. In further embodiments the detection molecules may be labeled with radioisotopes (e.g. $^{3}H$, $^{14}C$, $^{32}P$, $^{33}P$, $^{35}S$, $^{125}I$, $^{11}C$, $^{13}N$, $^{15}O$, $^{18}F$, $^{64}Cu$, $^{62}Cu$, $^{124}I$, $^{76}Br$, $^{82}Rb$, $^{68}Ga$ or $^{18}F$) or particles (e.g. gold). The different types of labels may be conjugated to a detection molecule using various chemistries, e.g. the amine reaction or the thiol reaction. However, other reactive groups than amines and thiols can also be used, e.g. aldehydes, carboxylic acids and glutamine. In a particularly preferred embodiment, the staining may be carried out with an anti EpCAM antibody connected to any of the mentioned fluorescent stains, more preferably to a FITC label. Further particularly preferred is the use of the Syto 9 stain for DNA or RNA molecules.

The activity may, in a further embodiment, be a mechanical manipulation of the cell. "Mechanical manipulation" as used herein refers to any exterior intervention with regard to a cell, a cell group or all or essentially all cells captured on a filter material according to the present invention. The exterior intervention may include a mechanical opening of the cells, a physical moving or rotating of the cells. Further envisaged are physical interventions due to the employment of electric currents, the flowing of liquids, the use of pressure, the employment of temperature increases or decreases with regard to a cell or group of cells. Such activities may be carried out, for example, by a robotic or semi-robotic entity, e.g. in the environment of a microfluidic system or cell preparation system.

The activity may, in a further specific embodiment, be a mechanical manipulation comprising a cell releasing activity. The term "releasing" as used herein refers to the extraction of one or more specific cells or groups of cells from a filter material. The extraction may be performed before, during or after a melting/solidification procedure, or before, during or after a staining or optical analysis procedure. For example, a cell detected by in vivo staining as potentially interesting or falling within the tested criteria, may be released from the filter material, subsequently transported to a different carrier, or medium e.g. culture medium and be analysed with different methodologies, or be cultured and amplified for subsequent analysis steps etc. The releasing of cells may be based on the use of position marker elements as defined herein above. For example, by saving the position marker code, or a corresponding coordinate, a cell may be identified or re-identified easily after an initial staining or detection step. For the release of cells micromanipulators or suction equipment may be used. Due to the advantageous result of the method according to the present invention to provide filter material comprising cells in a fixed position, subsequent analysis and extraction procedures are swiftly and accurately realizable.

The activity may, in a further embodiment, be a biological manipulation of the cell. "Biological manipulation" as used herein refers to the application of biological entities to the cells in order to affect their behavior, size, structure, histology etc. Examples of such biological manipulations include the application of biologic binding entities such as antibodies. Further examples include the provision of nutrients for the cells allowing the growth and mitotic division of the cells. Also envisaged is the employment of binding factors, such as ligands or growth factors, transcription factors, specific sugar classes, the use of cellular inhibitors or activators etc. Further biological manipulations would be known to the person skilled in the and are also envisaged by the present invention.

The activity may, in yet another embodiment, be a biochemical manipulation. A "biochemical manipulation" as used herein is understood as exposing a cell on a filter material according to the present invention to biochemically active entities, such as RNAi molecules, degrading enzymes, small molecules supposed to have specific molecular effects by binding to ligands or receptors, inducing molecular reactions etc. Biochemical manipulation may also include the performance of biochemical reactions in situ, e.g. the performance of polymerase chain reaction in situ, the detection of gene expression in situ or the of protein expression, the detection of the presence of protein, lipid, DNA/RNA, Fluorescence/Chromogenic In-Situ Hybridization (FISH/CISH), glycosidic structures or other entities within or on one or more cells etc. Further biochemical manipulations would be known to the person skilled in the and are also envisaged by the present invention.

In a further particularly preferred embodiment of the present invention, the activity comprises culturing the isolated cell(s). The cells captured on a filter material which is preferably deposited on a phase-change medium comprising a porous, mesh-like, open, or partially open structure, may be provided with growth medium or nutrients, e.g. carbon sources such as sugars, nitrogen sources, vitamins, hormones, growth factors, salts, trace minerals, proteins etc. The culturing may be adapted to the cells captured, e.g. to bacterial cells, to human cells, to epithelial cells etc. In further specific embodiments, the growth medium may be a minimal medium, a selective medium, or be enriched with labels for subsequent analyses, e.g. radioactive or fluorescent labels, or dyes etc. The culturing itself may be performed by passing or flowing the growth medium below the captured cells, e.g. within the layer of phase-change medium comprising cavities or openings. The flowing may be a constant flowing provided by a tubing or fluidic system comprising valves or movement units, reservoirs, recycling or replacement units etc. In a specific embodiment, the culturing may be carried out in a microfluidic environment. Furthermore, the culturing may be carried out at suitable temperatures, e.g. at temperature suitable for the growth of the capture cells, e.g. at a range of 28 to 40° C., preferably at 37° C. By modifying the incubation temperature, cells may further be induced to molecular reactions, which can subsequently be detected optically. The culturing may be carried out for any suitable time, e.g. for a time period of 30 min to several weeks.

In a further particularly preferred embodiment of the present invention the cell to be isolated or captures is a rare cell. The term "rare cell" as used herein refers to the relative frequency of occurrence of the cell within a group of other cells. For example, a rare cell may be a cell being present in a ratio of one cell versus $10^6$, $10^7$, $10^8$, $10^9$ or more cells within a sample volume of about 1 ml. A particularly preferred rare cell is a circulating tumor cell, in particular an epithelia tumor cell transported through the blood stream of a human being or a mammal or higher eukaryote. In further specific embodiments, a captured cell may be a tumor cell such as a breast cancer cell, lung cancer cell, urothelial cancer cell, urinary bladder cancer cell, sarcoma cell, prostate cancer cell, or non-small cell lung cancer cell.

In further preferred embodiments, the cell may be a bacterial cell, e.g. a bacterium of the genus *Neisseria*, such as *Neisseria meningitidis*, a bacterium of the genus *Streptococcus*, e.g. *S. pneumoniae*, a bacterium of the genus *Staphylococcus*, e.g. *S. aureus*, a bacterium of the genus *Haemophilus*, e.g. *H. influenza*, a bacterium of the genus *Escherichia*, e.g. *E. coli*, or a bacterium of the genus *Mycobacterium*, e.g. *M. tuberculosis* or *M. leprae*.

In a further preferred embodiment of the present invention, the optical imaging or optical analysis of cells processed according to the methods of the present invention may be performed with suitable microscopes and microscopy technologies. Examples of such microscopy techniques include bright field microscopy, dark field microscopy, phase contrast microscopy, differential interference contrast microcopy, fluorescence microscopy, atomic force microscopy, super resolution microscopy and confocal laser scanning microscopy. It is a particularly advantageous aspect of the present invention that the cells processed according to the herein described methodology can be imaged or visualized in an improved quality on the basis of simple, widely known, versatile and easy to implement bright field microscopy. The described cell processing is further well suited for imaging approaches using other microcopy techniques. It is within the skilled person's capabilities, adapting certain features and parameters of the present methodology to the microscopy approach selected. For example, the staining, the use of fluorescent markers, the wavelength of excitation and detection etc. may be adapted, the carrier may be adapted. Furthermore, in specific embodiments a cover slip may be used in order to cover the processed cells on the filter material.

In a further aspect the present invention relates to processed filter material comprising isolated cells suitable for optical imaging, which is obtainable by a processing method as used herein. The filter material may accordingly comprise captured cells after a melting and solidification process as described herein, which are located in one optical plane. The filter material may be used for optical analysis, or be subjected to additional staining or manipulation steps. Accordingly provided filter material may further be used for life prolonging actions with regard to the captured cells. The filter material may thus be contacted with growth medium as define herein, or it may be stored in a cool environment, e.g. in a refrigerator or cooling room. Alternatively, the filter material may be frozen, e.g. at −20° C. or at −80° C. to preserve it for subsequent analysis steps. Before freezing, the filter material may be prepared for freezing conditions, e.g. by adding suitable freezing medium as known to the person skilled in the art.

In yet another aspect of the present invention, the processed filter material obtained according to methods as described herein may be used for any suitable diagnostic, or analytic test. It may, for example, be used for histological examination, preferably after staining steps as described herein. Furthermore, it may be used for microbiological or virological analysis, e.g. the identification and characterization of captured bacteria or viruses. In further embodiments, it may be used for biochemical purposes, e.g. for the identification and selection of active small molecules providing effects on captured cells, the test of inhibiting or inducing molecules on the captures cells, the testing of biochemical modifications with regard to the metabolism, structure of viability of a cell etc. The processed filter material may, in particularly preferred embodiments, be used for oncologic analyses, e.g. the detection and characterization of captured rare cells such as circulation tumor cells. The cells may, for example, be identified according to the binding of antibodies to surface marker and the concomitant or subsequent staining with fluorescent dyes, or the staining with compartment specific dyes for DNA or RNA in order to analyse mitotic activity. In a further particularly preferred embodiment, the processed filter material may be used for hematologic analyses. Accordingly, the processed filter material cell may be derived from blood samples comprising, for example, white blood cells, or specific leukocyte types or classes. The cells may accordingly be analysed for their frequency, size, viability etc.

In yet another aspect the present invention relates to a device for processing cells to render them suitable for optical imaging, comprising (a) a filter material for capturing a cell as defined herein above, (b) a layer of phase-change medium as defined herein above; and (c) a heating and/or cooling unit. The device may, in one embodiment, comprise a filter material which is removable, e.g. transferable to a filtration unit or be inserted into a filtration device, wherein one or more cells, preferably rare cells as defined herein above, or any other cell type such as a bacterial cell as defined herein above are captured on the filter material. The capturing of the cells may also be performed by different methods, e.g. via selective binding to binding molecules such as antibodies, immunomagnetic isolation procedures etc. Subsequently, the filter material may be reintroduced into a device for processing cells according to the present invention.

In another embodiment, the filter material for capturing cells may already be provided or present together with captured cells on it, e.g. after having performed a filtration or cell capturing process in an independent device or in a filtration unit, or another capturing procedure as mentioned herein. In specific embodiments, the device may comprise more than one filter material, e.g. 2, 3, 4, 5, 6, 7, 10, 15 or more filter materials or filters, allowing for a parallel, or semi-parallel processing. Also sequential processing of more than one filter material or filter is envisaged by the present invention.

In a further embodiment, the device may comprise an insertion slot, notch or introduction zone, which allows for the insertion of filter material or filters comprising one or more captured cells. Such a zone may be equipped for rapid introduction of filters and their removal after the processing steps, i.e. as optically flat filter material comprising cell(s) at a fixed position. In specific embodiments, the device may comprise more than one insertion slot, notch or introduction zone, e.g. 2, 3, 4, 5, 6, 7, 10, 15 or more insertion slots, notches or introduction zones, allowing for a parallel, or semi-parallel processing. Also sequential processing in said insertion zones is envisaged.

In another embodiment of the present invention, the device as defined herein comprises one or more layers of phase-change medium as defined herein above. These layers of phase-change medium may, for example, be provided in a reservoir or magazine compartment and be associated with a filter material upon the introduction of the filter material comprising cells into the device. Alternatively, the device may provide for an external replenishment of phase-change medium after the completion of processing procedure for one or more than one filter. The phase-change medium may, for example, be stored in a ready to use fashion in a suitable environment and be introduced into the device upon starting of a new processing cycle. This may preferably be performed automatically, e.g. by using robotic techniques, or via an automated delivery system. In further embodiments, the phase-change medium may be provided in a melted form, e.g. be kept in a hot reservoir or heating unit and be cast into a mold, preferably as described herein above, upon starting of a processing cycle. This can be repeated in every cycle of the processing scheme. The mold may accordingly be removed after the phase-change medium has solidified. Reservoirs for melted phase-change medium may, in specific embodiments, also be part of a device according to the present invention. These reservoirs may, alternatively, be removable and only be associated with the device when needed.

In further, specific embodiments, the device may also provide for the presence of carriers as defined herein above. For example, the device may comprise a magazine compartment or delivery system for carriers, which may be associated with a filter material and a phase-change medium upon the introduction of the filter material comprising cells into the device. Alternatively, the carrier material may be already connected to the phase-change medium and be associated (as combination) with the filter material upon its introduction into the device. It is also preferred that pre-manufactured carrier-phase-change medium bundles or packets are provided in the device, e.g. in a magazine compartment. Upon the starting of a processing cycle, a carrier-phase-change medium packet may be inserted into the processing site. The packet may be kept in a suitable environment, e.g. in cool environments or dry environments etc.

In further embodiments of the present invention, the phase-change medium, or a combination of the phase-change medium and a carrier may be provided in a culturing or cell growth-allowing environment in the device. The device may accordingly be provided with tubes or joints; and/or it may comprise reservoirs and repositories for liquids, e.g. water, chemicals, ingredients, nutrients, growth factors, carbon or nitrogen sources etc. or any other entity to be used for culturing cells such as a temperature control unit and a $CO_2$ supply. The device, may, for example be integrated in a fluidic or microfluidic system comprising the above indicated connections and reservoirs. Also included may be units for controlling the flow of liquids, the pH, the temperature, the concentration of molecules etc. In further embodiments, a culturing unit as described above may be removable from the device and accordingly be used upon necessity, e.g. when processing living cells.

In a further preferred embodiment, a device as defined herein may comprise a unit, which is able to heat a filter material and an associated phase-change medium, in particular in order to provide the possibility of melting a phase-change medium as defined herein above. In further embodiments, the device may additionally comprise a cooling unit, in particular in order to provide the possibility of enhancing the solidification process as described herein. In further embodiments, the heating or cooling unit may additionally be usable for controlling the temperature of culturing steps in the device. The cooling device may further be used for an in situ conservation of processed filter material according to the present invention. Such a conservation may, for example, be refrigeration in situ until a subsequent staining procedure or an optical imaging analysis is carried out. The processed filter material may, for example, be cooled to a temperature of about 4-8° C. Also envisaged is the presence of a freezing unit within the device, which allows for a freezing of processed filter material as described herein. Frozen filter material may either be kept in situ, or be removed from the device in order to be stored in a freezer, e.g. at −80° C., or −20° C. or at any other suitable temperature. In further embodiments, a freezing or cooling unit as described above may be removable from the device and accordingly be used upon necessity, e.g. when storage of the filter material is required.

In a particularly preferred embodiment, the cooling or heating unit may be a Peltier element, allowing for heating and cooling activities.

In another preferred embodiment of the present invention, a device as defined herein above may comprise a filtration or capturing unit allowing for isolation or capturing of cells onto a filter material as defined herein above. The filtration or capturing unit may, for example, be capable of providing a pressure onto or liquid flow of sample material leading to a forced passage through a filter material as defined herein above. Alternatively, the capturing unit may be equipped with magnetic beads, or immunologic elements etc. allowing for an immune-magnetic or immunological selection of cells.

It is particularly preferred that the device as defined above comprises a removable pressure delivery system. The system may, in one embodiment, be directly coupled to the filter material. In one specific embodiment, the removable pressure delivery system may be a needle connected to a vacuum or low pressure generating unit, e.g. a vacuum pump. The needle may be removable from the filter material, or the compartment where the filter material is located after having performed a filtration or cell isolation step.

In further specific embodiments, a removable pressure delivery system as described above may be implemented in order to remove water or liquid residues from the filter material, e.g. ethanol rests.

Furthermore, the device according to the present invention may have a compartment or nested compartment structure. An example of an envisaged compartment structure is provided in FIG. 5B with FIG. 5A showing a possible phase-change medium to be used in the device. Such an integrated device form may be combined with additional units as described herein above or below, e.g. temperature units, reservoirs, magazine units, tubes etc.

It is particularly preferred that a device as defined herein above comprises a means for transporting a filter material as defined herein above to a carrier as defined herein above. Such a transportation unit may be a robotic entity or a delivery system. Also envisaged are semi-automatic transporting means. It is further particularly preferred that a device as defined herein above comprises a means for transporting a layer of phase-change medium to a carrier as defined herein above. Such a transportation unit may be a robotic entity or a delivery system. Also envisaged are semi-automatic transporting means.

In further embodiments of the present invention, a device as defined above may be connected to downstream processing and/or analysis units or equipment. For example, the device may be equipped with staining, fixation, mechanical manipulation, biological manipulation and/or biochemical manipulation units, or entries or exits allowing for such an activity. Details of possible activities which may be carried out in, or by such units are provided herein above. Furthermore, the device may be connected to an optical imaging system, e.g. a microscope. Examples of microscopes which may be associated with or integrated in the device of the present invention include a bright field microscope, a dark field microscope, a phase contrast microscope, a differential interference contrast microscope, a fluorescence microscope, an atomic force microscope, a confocal laser scanning microscope and a super resolution microscope. Further envisaged is the presence of light sources, optical filters, camera units and other elements necessary for optical imaging. Preferably, the device may also be equipped with a control unit or computer unit allowing for the performance, supervision and orchestration of device activities. The control unit may further have a user interface allowing for the programming, supervision and configuration of the device. Furthermore, the device may be provided with an internet or intranet interface allowing for remote controlling etc. Also envisaged is the use of an image capturing and storage unit, e.g. in the form of a computer device. This image capturing and storage unit may further be equipped with suitable analysis software or programs allowing for a characterization of cells or cell histology, or for diagnostic analysis procedures, e.g. in the case of tumor cells. Also envisaged is the use of microbiological identification programs in case bacterial cells or viruses are analysed.

In yet another aspect the present invention relates to a method for producing optical flat filter material. The method comprises the steps of melting a phase-change medium as defined herein above until the medium is spread out below the filter material; and lowering the temperature of the phase-change medium until the medium solidifies, resulting in an optically flat filter. In a preferred embodiment, the method is performed with filter material comprising captured or isolated cells, e.g. rare cells or bacterial cells as defined herein above. The method may, in specific embodiments, also be used for the preparation of filter material comprising elements such as virus particles, inorganic entities such as metal, wood, plastic or other material, e.g. micrometer dimensioned pieces of such material derived from accidents, quality control measurements, product testing measurements etc.

In yet another aspect the present invention relates to a method for producing a phase-change medium suitable for the present methodology. The method comprises steps of cutting our or carving out cavities from a block of solid phase-change medium. The phase-change medium may accordingly be provided with a porous, mesh-like, open, or partially open structure, one or more channels, one or more passages or one or more pipe elements. The cutting out may, for example, be performed by a laser or laser device. The channels or passages may have a connection with the margin(s) of the phase-change medium and/or have contact with the outside of the phase-change medium. Furthermore, the passages, openings etc. may be interconnected. It is preferred that the openings allow for a suitable flow of liquids, in particular growth or culturing medium below or in the vicinity of cells captured on a filter material. In a further embodiment the method may comprise the step of casting the phase-change medium in a melted or liquid state into a corresponding mold and letting the material subsequently be solidified, followed by the extraction of the mold.

The following examples and figures are provided for illustrative purposes. It is thus understood that the example and figures are not to be construed as limiting. The skilled person in the art will clearly be able to envisage further modifications of the principles laid out herein.

EXAMPLES

Example 1

Preparation of MCF7 (Breast Cancer) Cells

The Filtering Procedure

A 75 cm$^2$ cell culture flask (Nunc) with 90% confluent MCF7 cells was trypsinized (Trypsin+EDTA, Invitrogen) for 6 minutes and resuspended in RPMI1640 medium supplemented with FBS, Penicillin/Streptomycin and Glutamax (Invitrogen). The cells are then washed once by means of centrifugation (5 min, 1000 RPM) and resuspended in 10 ml DPBS (invitrogen). The cell suspension is diluted in such a way that the cells will cover about 10% of the available filter area in 10 ml of DPBS. A glass micro-analysis filter holder (Millipore) was used to filter 10 ml of cell suspension by applying a modest vacuum in the flow through compartment.

Preparation and Visualisation of the Filter

Figure 2A:
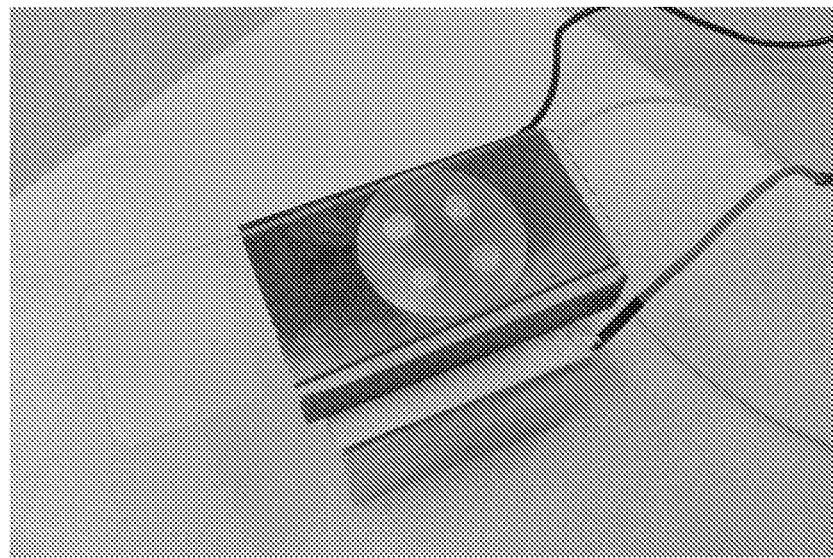
FIG. 2 shows a Peltier element which melts paraffin structures supporting a polycarbonate filter (FIG. 2A) which after cooling down results in an optically flat and fixed filter surface (FIG. 2B).
Figure 2B:
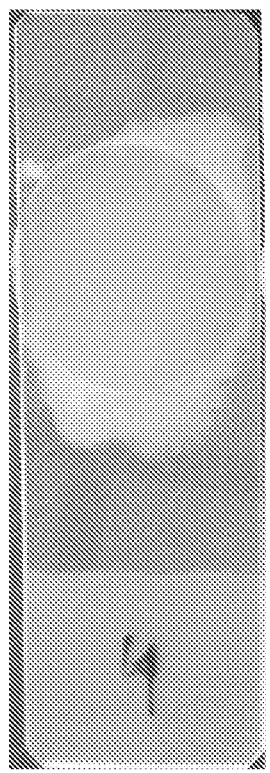
Figure 3A:
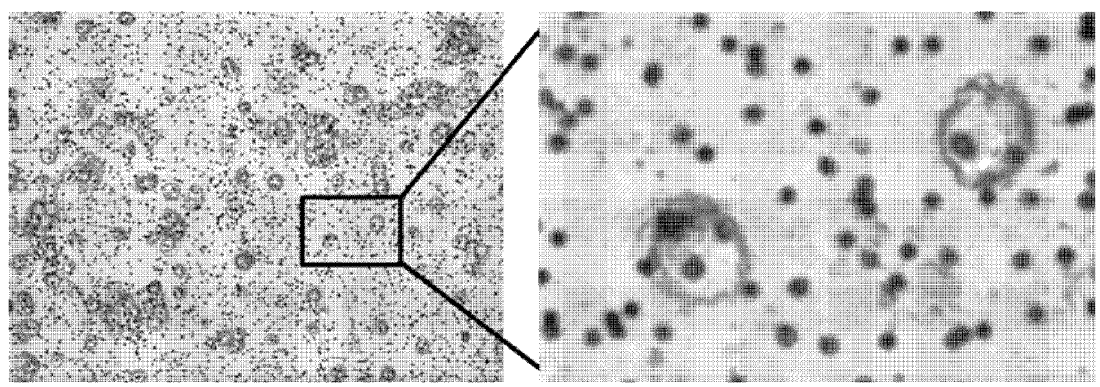
FIG. 3A shows MCF7 (breast cancer) cells on top of a polycarbonate filter (Whatman Cyclopore track etched membrane) with 8 μm pores (small black dots) after melting of a paraffin support structure.
Figure 3B:
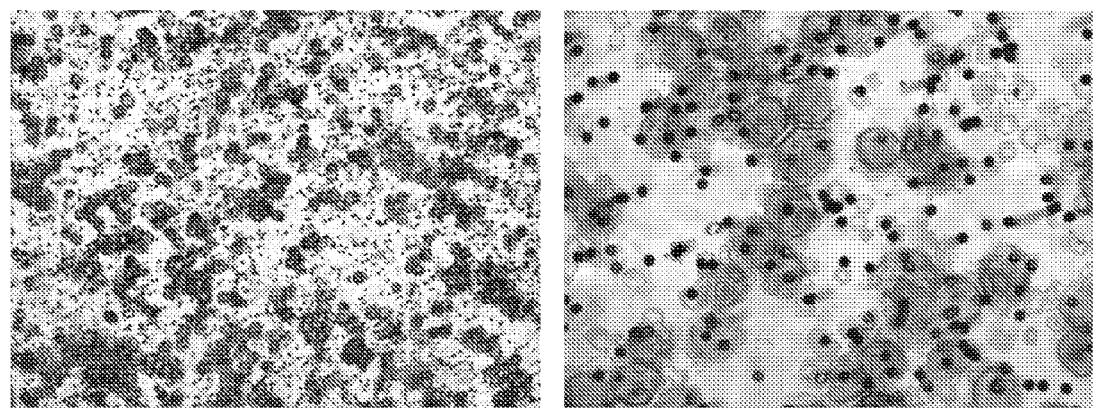
FIG. 3B shows MCF7 (breast cancer) cells on top of a polycarbonate filter (Whatman Cyclopore track etched membrane) with 8 μm pores (small black dots) after melting of a paraffin support structure and subsequent H&E staining The cells remain on the filter and the filter remains attached to the microscope slide via the paraffin throughout the staining protocol.

The filter was subsequently removed from the filter holder and placed on top of a standard microscope slide with 20 µl solid paraffin wax deposited on it. The microscope slide was the transferred to a peltier element, which provided the heat to melt the paraffin wax (see FIG. 2A). At the moment that the paraffin was completely molten, the microscope slide was removed and cooled at room temperature until the paraffin had re-solidified (see FIG. 2B). The slide was then either imaged on a standard microscope (Zeiss) using reflected light (see FIG. 3A) or entered a standard Hemotoxilin and Eosin (H&E) staining procedure (see FIG. 3B). The latter providing even more contrast.

When processed according to the above outlined procedure the filter remained perfectly attached to the paraffin layer and the cells remained perfectly attached to the filter (either with of without fixation prior to the staining procedure). This is remarkable because the H&E protocol requires hundreds of dips in to several different fluid containers and flushing under running tap water. The biological cells were imaged with a very high image quality. The high image quality is caused by the optically flat surface and by the fact that the solidified paraffin wax layer acts as a very good light diffuser.

Example 2

A Meltable Filter Support Structure with Integrated Flow System

By pipetting about 400 µl molten paraffin into a large volume of hot water which subsequently is allow to cool down, thin, flat, homogeneous patches of paraffin were created. Using a hot stamp a circle was punched out of the patch onto a microscope slide (1). The inner part of the circle was removed using a smaller circular cold stamp (2). A needle was then heated and fixed into the side wall of the circular support structure (3, 4). The filter was applied (5) and using the large hot stamp the filter was sealed onto the ring support structure (6) using the large hot stamp (1). By applying a vacuum to the needle a low pressure was generated in the compartment below the filter allowing for filtration processes to take place (see FIG. 4).

Pressure of vacuum can also be applied by other means than a needle, e.g. by pores or holes in the substrate material, or by pores or holes in the supporting paraffin wax. The filter material (with cells) can be attached to the microscope slide by heating. The heating causes the paraffin wax to melt and attract the filter to the microscope slide (as in Example 1).

Because the cells are fixed with respect to the filter and the microscope slide, the same cell(s) can be located before and after a treatment.

The invention claimed is:

1. Method for processing isolated cells to render them suitable for optical imaging, comprising the following steps:
   (a) depositing filter material comprising captured cells on a phase-change medium, said phase-change medium being mounted on a carrier;
   (b) melting said phase-change medium until the medium is spread out below said filter material; and
   (c) lowering the temperature of said phase-change medium until the medium Solidifies, resulting in a filter comprising said cells in a single optical plane and at a fixed position.

2. The method of claim 1, additionally comprising the initial step of capturing a cell on a filter material.

3. The method of claim 1, wherein said filter material is capable of size excluding cells to be isolated from a fluid or solution having a pore size of about 0.5 to 20 µm and wherein said filter material is a polymer filter.

4. The method of claim 1, wherein said phase-change medium is a medium which melts and solidifies in a temperature range of about 25° C to 70° C.

5. The method of claim 1, wherein said phase-change medium comprises a porous, mesh-like, open, or partially open structure and/or comprises channel, passage or pipe elements, wherein said structure or elements allow the passage of a fluid through said medium.

6. The method of claim 4, wherein said medium is a hydro wax.

7. The method of claim 1, wherein said carrier is a glass carrier or a polymer material carrier, and wherein said carrier comprises a position marker.

8. The method of claim 1, wherein said method comprises as additional step an activity selected from the group of staining, fixating, releasing, mechanically manipulating, biologically manipulating and biochemically manipulating said isolated cell(s).

9. The method of claim 8, wherein said activity comprises culturing said isolated cell(s) via flowing a nutrient fluid through a porous, meshlike, open, or partially open phase-change medium.

10. The method of claim 1, wherein said cell is a circulating tumor cell, or a bacterial cell.

11. The method of claim 1, wherein said optical imaging is bright field microscopy, dark field microscopy, phase contrast microscopy, differential interference contrast microcopy, fluorescence microscopy, atomic force microscopy, confocal laser scanning microscopy or super resolution microscopy.

12. A method for optical imaging for diagnostic, histological, microbiological, biochemical, oncologic, or hematologic analysis comprising the step of imaging a processed filter material comprising isolated cells which is obtained by the method according to claim 1.

13. Device for processing cells to render them suitable for optical imaging, comprising:
   (a) a filter material configured to capture a cell;
   (b) a removable pressure delivery system coupled to the filter material configured to isolate cells onto the filter material;
   (c) a layer of phase-change medium;
   (d) a means for transporting said filter material and/or said layer of phase-change medium to a carrier;
   (e) a heating unit configured to melt said phase-change medium until the medium is spread out below said filter materials; and
   (f) a cooling unit configured to lower the temperature of said phase-change medium until the medium solidifies and provides a filter comprising said cells in a single optical plane and at a fixed position.

* * * * *